(12) United States Patent
Hill et al.

(10) Patent No.: US 9,173,737 B2
(45) Date of Patent: Nov. 3, 2015

(54) STENTED HEART VALVE DEVICES

(75) Inventors: Alexander J. Hill, Blaine, MN (US);
Mark J. Capps, Mission Viejo, CA (US); Carol E. Eberhardt, Fullerton, CA (US); Morgan M. House, Newfields, NH (US); Stuart R. MacDonald, Haverhill, MA (US); Joseph C. Morrow, Eden Prairie, MN (US); Jerald Redmond, Blaine, MN (US); Janice L. Shay, Lake Forest, CA (US); Timothy R. Ryan, Shorewood, MN (US)

(73) Assignee: Medtronic, Inc., Santa Rosa, CA (US)

( * ) Notice: Subject to any disclaimer, the term of this patent is extended or adjusted under 35 U.S.C. 154(b) by 0 days.

(21) Appl. No.: 12/428,737

(22) Filed: Apr. 23, 2009

(65) Prior Publication Data

US 2010/0036479 A1    Feb. 11, 2010

Related U.S. Application Data

(60) Provisional application No. 61/125,235, filed on Apr. 23, 2008.

(51) Int. Cl.
*A61F 2/82*    (2013.01)
*A61F 2/24*    (2006.01)

(52) U.S. Cl.
CPC ................ *A61F 2/2418* (2013.01); *A61F 2/24* (2013.01); *A61F 2/2412* (2013.01); *A61F 2/2487* (2013.01); *A61F 2210/0014* (2013.01); *A61F 2220/0016* (2013.01); *A61F 2230/001* (2013.01); *A61F 2230/005* (2013.01); *A61F 2230/008* (2013.01);

(Continued)

(58) Field of Classification Search
CPC ..................................................... A61F 2/2487
USPC ........................ 623/1.24, 1.26, 1.31, 2.1–2.19
See application file for complete search history.

(56) References Cited

U.S. PATENT DOCUMENTS 6,821,297 B2    11/2004   Snyders
7,704,277 B2     4/2010   Zakay et al.

(Continued)

FOREIGN PATENT DOCUMENTS

DE    200 03 874    6/2000
DE    100 10 074    4/2005

(Continued)

OTHER PUBLICATIONS

Bolling, et al., "Mitral Valve Reconstruction in the Patient with Heart Failure," Heart Failure Reviews, 6, 177-185, 2001.

(Continued)

*Primary Examiner* — Thomas J Sweet
*Assistant Examiner* — Rebecca Preston

(57) ABSTRACT

A stent frame including an annular portion having first and second ends, a central longitudinal axis, and a wire portion with at least two extending posts and a generally sinusoidal series of peaks and valleys between each of the at least two extending posts; an atrial portion extending from the first end of the annular portion, wherein the atrial portion includes a plurality of flares that extend radially outward relative to the longitudinal axis of the annular portion; and a ventricular portion extending from the second end of the annular portion, wherein the ventricular portion includes at least one flare that extends radially outward relative to the longitudinal axis of the annular portion.

23 Claims, 12 Drawing Sheets

(52) U.S. Cl.
CPC . *A61F 2230/0045* (2013.01); *A61F 2230/0054* (2013.01); *A61F 2230/0067* (2013.01); *A61F 2230/0076* (2013.01); *A61F 2250/0039* (2013.01)

(56) References Cited

U.S. PATENT DOCUMENTS

| | | | |
|---|---|---|---|
| 2002/0032481 A1* | 3/2002 | Gabbay | 623/2.11 |
| 2002/0123802 A1* | 9/2002 | Snyders | 623/2.18 |
| 2004/0019374 A1* | 1/2004 | Hojeibane et al. | 623/1.13 |
| 2004/0138745 A1* | 7/2004 | Macoviak et al. | 623/2.36 |
| 2004/0210304 A1* | 10/2004 | Seguin et al. | 623/2.11 |
| 2005/0203616 A1 | 9/2005 | Cribier | |
| 2006/0195183 A1* | 8/2006 | Navia et al. | 623/2.18 |
| 2007/0173932 A1 | 7/2007 | Cali et al. | |
| 2007/0198075 A1* | 8/2007 | Levy | 623/1.11 |
| 2008/0147183 A1 | 6/2008 | Styrc | |
| 2008/0208328 A1 | 8/2008 | Antocci et al. | |
| 2009/0005863 A1 | 1/2009 | Goetz et al. | |
| 2009/0276040 A1 | 11/2009 | Rowe et al. | |
| 2009/0281618 A1 | 11/2009 | Hill et al. | |
| 2009/0306768 A1 | 12/2009 | Quadri | |
| 2009/0319037 A1 | 12/2009 | Rowe et al. | |
| 2010/0030330 A1 | 2/2010 | Bobo et al. | |
| 2010/0036479 A1 | 2/2010 | Hill et al. | |
| 2010/0042147 A1 | 2/2010 | Janowsky et al. | |
| 2010/0217382 A1 | 8/2010 | Chau et al. | |

FOREIGN PATENT DOCUMENTS

| | | |
|---|---|---|
| DE | 102007043830 | 4/2009 |
| WO | 2005/067821 | 7/2005 |
| WO | 2006/027499 | 3/2006 |
| WO | 2007/071436 | 6/2007 |
| WO | 2008/028569 | 3/2008 |
| WO | 2009/033469 | 3/2009 |
| WO | 2009/053497 | 4/2009 |

OTHER PUBLICATIONS

Lozonschi, et al., "Transapical Mitral Valved Stent Implantation," Ann. Thorac. Surg., 2008;86:745-8.
Ma, et al., "Double-crowned valved stents for off-pump mitral valve replacement," Europ. J. of Cardio-thoracic Surg., 28 (2005) 194-199.
Massana, et al., "Conservative Surgery of the Mitral Valve. Annuloplasty on a new Adjustable Ring," Cardiovascular Surgery 1980, 1987: 30-37.
CA Examiner's Report, mailed May 7, 2015.

* cited by examiner

STENTED HEART VALVE DEVICES

CROSS-REFERENCE TO RELATED APPLICATION

This application claims the benefit under 35 U.S.C. §119 (e) of U.S. Provisional Patent Application No. 61/125,235, filed Apr. 23, 2008, which is incorporated herein by reference in its entirety.

TECHNICAL FIELD

The present invention relates generally to devices and methods for repair of heart valves, and more particularly to prosthetic heart valves for use in replacement of the mitral valve.

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the heart's ability to adapt to it, determine the treatment options that are available for a particular patient. In some cases, medication can be sufficient to treat the patient, which is the preferred option when it is viable; however, in many cases, defective valves have to be repaired or completely replaced in order for the patient to live a normal life.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, valve repair is sometimes either impossible or undesirable or has failed, such as in cases where dilation of the valve annulus is not the problem, leaving valve replacement as the preferred option for improving operation of the mitral valve. In cases where the mitral valve is replaced, the two general categories of valves that are available for implantation are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus mechanical valve recipients must take anti-coagulant drugs for life to prevent the formation of thrombus. On the other hand, the use of tissue valves provide the advantage of not requiring anti-coagulant drugs, although they do not typically last as long as a mechanical valve. Traditionally, either type of valve has been implanted using a surgical procedure that involves opening the patient's chest to access the mitral valve through the left atrium, and sewing the new valve in position. This procedure is very invasive, carries risks of infection and other complications, and requires a lengthy period of recovery for the patient.

To simplify surgical procedures and reduce patient trauma, there has been a recent increased interest in minimally invasive and percutaneous replacement of cardiac valves. Replacement of a heart valve in this way typically does not involve actual physical removal of the diseased or injured heart valve. Rather, a replacement valve is delivered in a compressed condition to the valve site, where it is expanded to its operational state. One example of such a valve replacement system includes inserting a replacement pulmonary valve into a balloon catheter and delivering it percutaneously via the vascular system to the location of a failed pulmonary valve. There, the replacement valve is expanded by a balloon to compress the native valve leaflets against the right ventricular outflow tract, thereby anchoring and sealing the replacement valve. In the context of percutaneous, pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Patent Application Publication No. 2003/0036791 A1 and European Patent Application No. 1057 460-A1.

Due to the different physical characteristics of the mitral valve as compared to the pulmonary valve, percutaneous implantation of a valve in the mitral position has its own unique requirements for valve replacement. There is a continued desire to be able to be able to improve mitral valve replacement devices and procedures to accommodate the physical structure of the heart without causing undue stress during operation of the heart, such as providing devices and methods for replacing the mitral valve percutaneously.

SUMMARY

One embodiment of the invention includes a compressible and expandable stent for implantation into a body lumen, such as for replacement of one of the atrioventricular valves. The stent comprises a frame having a central annular region, atrial flares extending from one side of the annular region, and ventricular flares extending from one portion of the opposite side of the annular region. Advantageously, the flares and other features of the stent frames of the present invention can be used to create stented valves that can accommodate large orifices and orifices having unusual shapes. With regard to placement within the relatively large mitral orifice, the stented valves of the invention can be implanted in such a way that no migration of the valve occurs and so that the left ventricular outflow tract is not obstructed. The stent frames of the invention are self-expanding and are used with a fabric covering to make a stent assembly. The valve can be either a pericardial construct or can use an animal valve. The delivery system used for such a stent assembly can consist of a catheter with a sheath at the distal end to maintain the stent assembly in a compressed state for delivery.

The invention further includes a method of positioning a valve into a body lumen, such as one of the atrioventricular valve openings of the heart. The method comprises the steps of compressing a stent frame of a stented valve, wherein the stent frame includes a central annular region, atrial flares, and ventricular flares. The stented valve is then delivered to the annulus of the desired valve area of the patient, which delivery may be performed transapically, for example. In one method, the valve is accessed through the bottom of the valve. When the valve is in position, the atrial region or portion of the stent is released, and then the delivery system is used to pull the stent valve back against the annulus to engage the atrial portion of the stent with the annulus. The ventricular portion of the stent is then released from the delivery system and the delivery system can be retracted from the patient.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
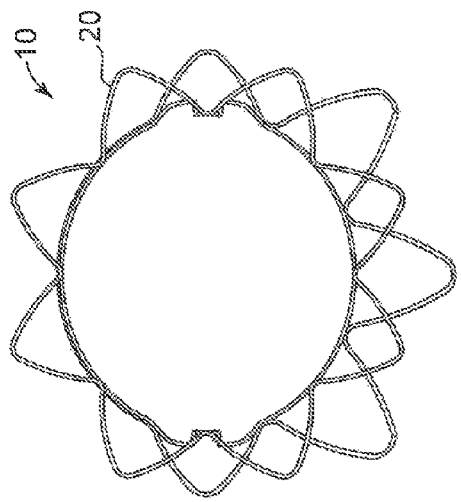
FIG. 1 is a perspective view of one exemplary embodiment of a stent frame in accordance with the invention.
Figure 2:
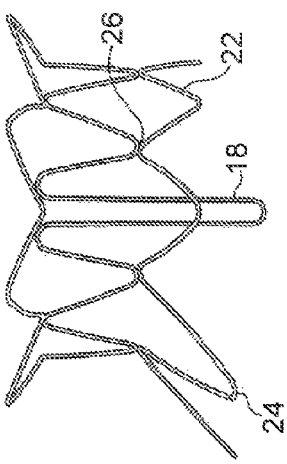
FIG. 2 is a top view of the stent frame of FIG. 1.
Figure 3:
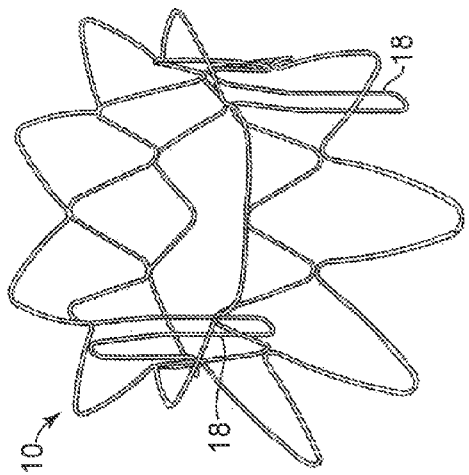
FIGS. 3 and 4 are different side views of the stent frame of FIG. 1.
Figure 4:
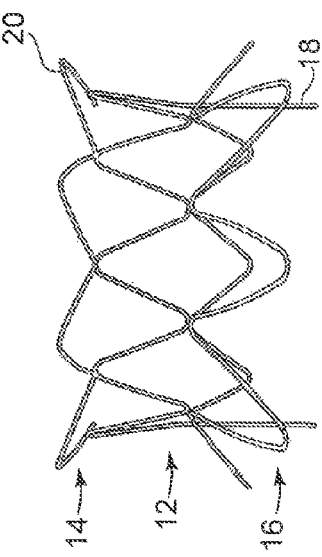
Figure 5:
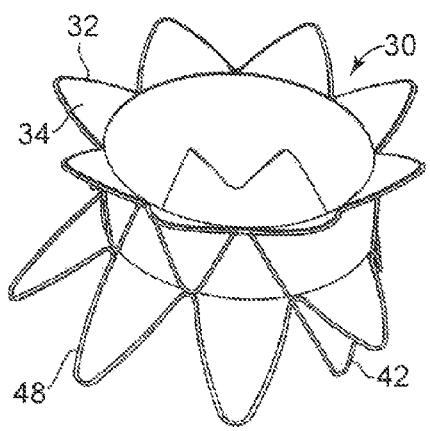
FIG. 5 is a perspective view of another stent frame including a different stent frame arrangement than the embodiment of FIGS. 1-4, and further illustrating fabric attached to the wires of the stent.
Figure 6:
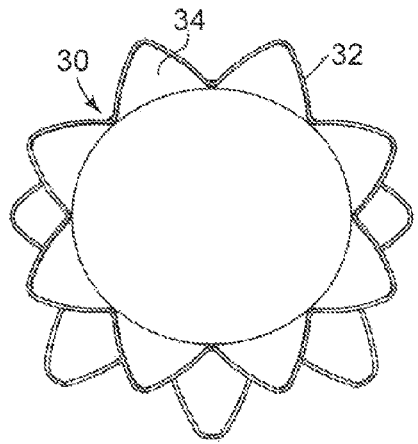
FIG. 6 is a top view of the stent frame of FIG. 5.
Figure 7:
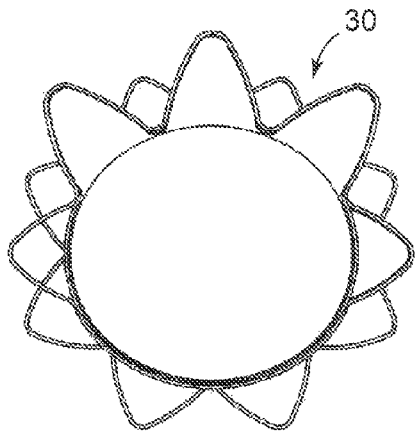
FIG. 7 is a bottom view of the stent frame of FIG. 5.
Figure 8:
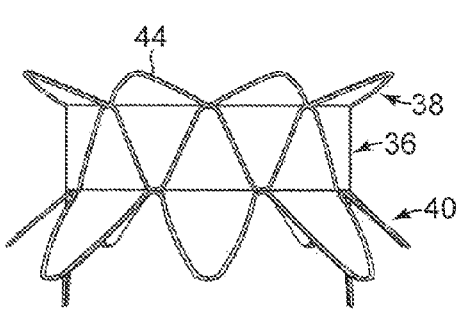
FIGS. 8 and 9 are different side views of the stent frame of FIG. 5.
Figure 9:
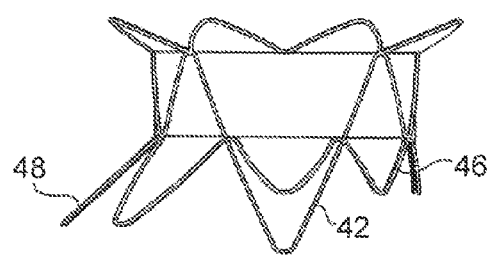
Figure 10:
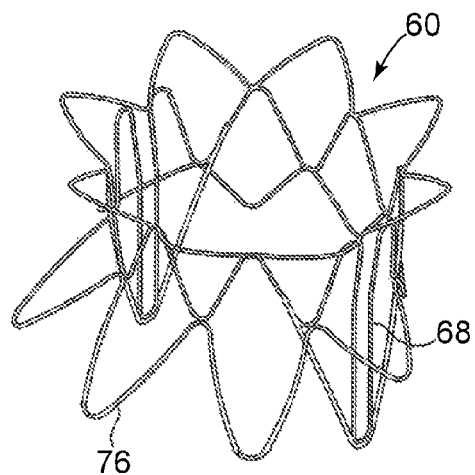
FIG. 10 is a perspective view of another stent frame in accordance with the invention.
Figure 11:
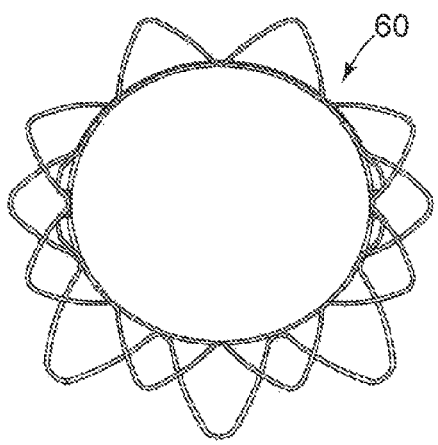
FIG. 11 is a top view of the stent frame of FIG. 10.
Figure 12:
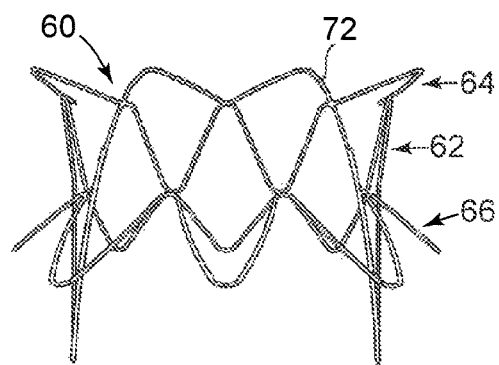
FIGS. 12 and 13 are different side views of the stent frame of FIG. 10.
Figure 13:
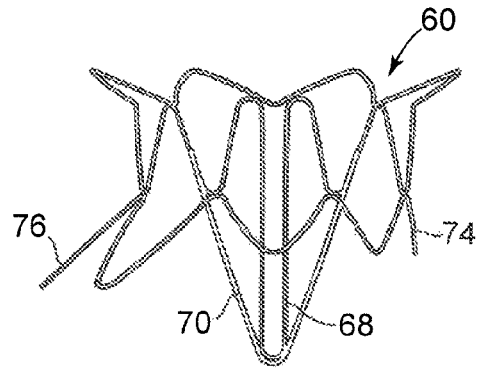
Figure 14:
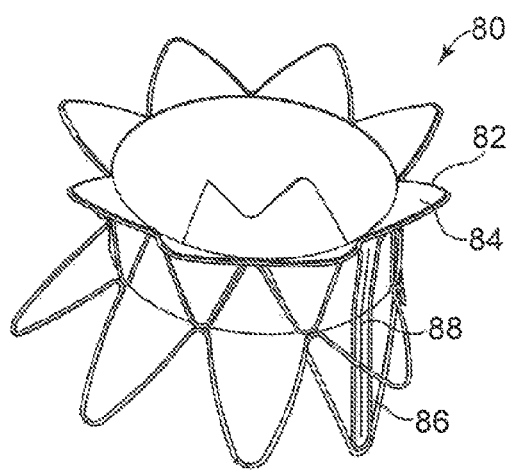
FIG. 14 is a perspective view of the stent frame of FIG. 10 with fabric attached to portions of the stent frame.
Figure 15:
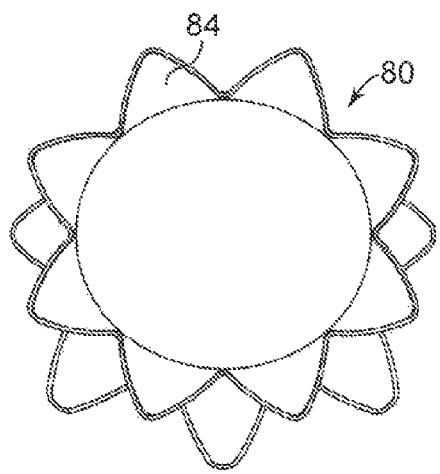
FIG. 15 is a top view of the stent frame of FIG. 14.
Figure 16:
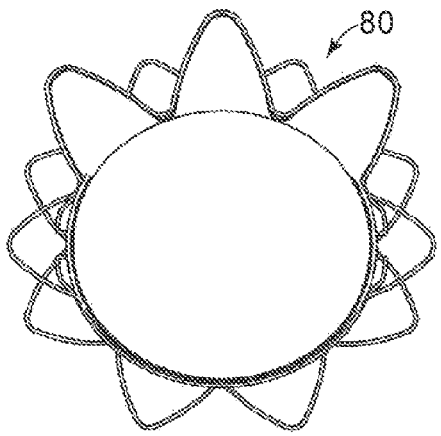
FIG. 16 is a bottom view of the stent frame of FIG. 14.

Referring now to the Figures, wherein the components are labeled with like numerals throughout the several Figures, and initially to FIGS. 1-4, one embodiment of an exemplary stent frame 10 in accordance with the invention is illustrated. Although the stents of the invention, such as stent frame 10, are primarily described herein as being used for mitral valve replacement, it is understood that many of the features of these stents can also be used for valves in other areas of the heart. For example, the stents of the invention may be used in the replacement of the tricuspid valve, where the configuration of such a stent may be identical or slightly different than described herein for replacement of the mitral valve due to the different anatomy in that area of the heart. In any case, the stents of the invention desirably restore normal functioning of a cardiac valve, and are intended for percutaneous implantation to take advantage of the benefits of this type of surgery. However, the stents described herein may instead be implanted using surgical techniques that include minimally invasive methods or more traditional open-heart surgical methods.

Exemplary embodiments of the stent frames of the invention are shown and described relative to the figures, such as stent frame 10. These stent frames may be fabricated of platinum, stainless steel, Nitinol, or other biocompatible metals or combinations of metals. The stent frames of the invention may alternatively be fabricated using wire stock, or the stent frames may be produced by machining or laser cutting the stent from a metal tube, as is commonly employed in the manufacturing of stents. The number of wires, the positioning of such wires, and various other features of the stent can vary considerably from that shown in the figures, while remaining within the scope of the invention.

In any case, the stent frames of the invention are preferably compressible to a relatively small diameter for insertion into a patient, but are also at least slightly expandable from this compressed condition to a larger diameter when in a desired position in the patient. It is further preferable that the process of compressing the stents does not permanently deform the stents in such a way that expansion thereof would be difficult or impossible. That is, each stent should be capable of maintaining a desired structural integrity after being compressed and expanded. In one preferred embodiment of the invention, the wires that make up each of the stent frames can be formed from a shape memory material, such as a nickel titanium alloy (e.g., Nitinol). With this material, the stent frame can be self-expandable from a contracted state to an expanded state, such as by the application of heat, energy, or the like, or by the removal of external forces (e.g., compressive forces). The stent frame should be able to be repeatedly compressed and expanded without damaging the structure of the stent frame. In addition, the stent frame may be laser cut from a single piece of material, as described above, or may be assembled from multiple components or wires. For these types of stent structures, one example of a delivery system that can be used includes a catheter with a retractable sheath that covers the stent and its associated valve structure until it is to be deployed, at which point the sheath can be retracted to allow the stent frame to expand. Further details of such a delivery process with stent frames of the present invention are discussed in further detail below.

The stent frames of the invention will preferably be used as a part of a stented valve assembly that includes a valve material attached within the inner area of the stent frame to form leaflets. These stented valve assemblies of the invention may use a preserved native porcine aortic valve or other vessels or donor species. In order to provide additional valve strength in the relatively high-pressure conditions that exist in the mitral valve area of the heart, and/or to provide greater flexibility in designing a valve with a particular size and/or shape, pericardial valves may alternatively be assembled in a tricuspid or bicuspid leaflet configuration.

Referring again to FIGS. 1-4, stent frame 10 generally includes an annular portion 12, an atrial portion 14 extending from one end of the annular portion 12, and a ventricular portion 16 extending from the opposite end of the annular portion 12. Annular portion 12 includes a wire structure that is shaped in a generally sinusoidal configuration around its perimeter. More particularly, annular portion 12 includes two extending posts 18 on generally opposite sides of its perimeter, and a sinusoidal pattern having a generally constant height between each of the extending posts 18. This annular portion 12 is shown as being formed by a single wire, although it is contemplated that a number of different wires or stent frame components may be assembled to make up this annular portion 12. It is further contemplated that the entire stent frame 10 is cut from a single sheet of material such that annular portion 12 is part of an integral structure that does not include individual components. The extending posts 18 are shown as having a greater height than the portion of the annular portion 12 between the posts 18, where the relative size difference between these parts of the annular portion 12 can be the same or substantially different than shown. In any case, the height of each of the extending posts 18 is designed to provide an attachment area for the leaflet of a valve that will be attached within the stent frame 10. Thus, this embodiment of the stent frame 10 that has two extending posts 18 is designed to accommodate a bi-leaflet valve; however, it is contemplated that the annular portion 12 instead can comprise three extending posts 18 to accommodate attachment of a tri-leaflet valve.

It is further contemplated that the stent frame can alternatively or additionally include one or more extending posts that extend in the opposite direction than discussed above relative to the extending posts 18. These extending posts can extend toward the atrial portion of the stent rather than the ventricular portion of the stent.

Atrial portion 14 includes a wire structure that is shaped to provide a series of flanges 20 that extend radially outward at an angle around the periphery of one end of the annular portion 12. This atrial portion 14 is shown as being formed by a single wire, although it is contemplated that multiple wires or stent frame components may be assembled to make up this atrial portion 14, or that the entire stent frame 10 is cut from a single sheet of material such no individual wires are used in the construction thereof. As shown, all of the flanges 20 are generally the same size and shape and extend at generally the same angle from the annular portion 12, although it is contemplated that the flanges 20 are configured differently from each other. The flanges are provided for engagement with one side of the annulus in which the stent frame 10 will be implanted, thus, the flanges 20 can be provided with a number of different configurations to meet the particular requirements of the locations in which the stent frame may be implanted. For example, the atrial portion 14 may have more or less flanges 20 than shown, the flanges 20 can extend at a greater or smaller angle than shown relative to the generally cylindrical shape of the annular portion 12, the flanges 20 can be longer or shorter than shown, and the like.

Ventricular portion 16 includes a wire that is arranged to provide a first portion 22 that extends in generally the same longitudinal or axial direction as the annular portion 12 along a portion of its periphery, and at least one flange 24 that extends radially outward at an angle relative to the annular portion 12. This ventricular portion 16 is shown as being formed by a single wire, although it is contemplated that multiple wires or stent frame components may be assembled to make up this ventricular portion 16, or that the entire stent frame 10 is cut from a single sheet of material such no individual wires are used in the construction thereof. As shown, the first portion 22 of the ventricular portion 16 is a series of sinusoidal peaks and valleys that are generally the same size and shape as each other, although it is contemplated that they are configured differently from each other. This first portion 22 generally follows the outer periphery of the annular portion 12 in the axial direction of the stent frame (i.e., there is little to no flare of this portion 22 relative to the annular portion 12), where the "peaks" of the wires of portion 22 meet the "valleys" of the annular portion 12, such as at an intersection point 26, for example. Such intersection points can occur around the periphery of the stent frame 10. It is further contemplated that the portion 22 can be flared at least slightly relative to the annular portion 12 in order to engage with the aortic leaflet (i.e., the aortic portion of the ventricular flare) without substantially blocking the left ventricular outflow tract.

The ventricular portion 16 further includes at least one flange 24 that extends or flares outwardly from the annular portion 12 on one side of the stent frame 10. Each flange 24 is provided for particular engagement with an annulus in which the stent frame will be implanted, such as the posterior side of a mitral annulus. In this embodiment, the portion 22 of the ventricular portion 16 does not flare outwardly on the anterior side so that it will not obstruct the left ventricular outflow tract when implanted in the mitral position. Because the flanges 24 are provided for engagement with one side of the annulus in which the stent frame 10 will be implanted, the flanges 24 can be provided with a number of different configurations to meet the particular requirements of the location in which the stent frame may be implanted. In particular, the ventricular portion 16 may have more or less flanges 24 than shown, the flanges 24 can extend at a greater or smaller angle than shown relative to the periphery of the annular portion 12, the flanges 24 can be longer or shorter than shown, and the like.

As discussed above, the stent frame 10 may comprise a single piece construction, such as a structure that is cut from a single piece of material, or may instead include a series of wires or wire segments that are attached to each other around the periphery of the stent frame 10. In either case, the wire portions of the annular portion 12, the atrial portion 14, and the ventricular portion 16 may have the same thickness or different thicknesses from each other. In one exemplary embodiment, the annular portion 12 comprises relatively thick wire portions, while the atrial portion 14 and ventricular portion 16 comprise relatively thin wire portions. In such an embodiment, the thickness of the wires that make up the atrial portion 14 and ventricular portion 16 may be the same or different from each other.

FIGS. 5-9 illustrate a stent assembly 30 in accordance with another embodiment of the invention. Stent assembly 30 includes a stent frame 32 and a covering material 34. Stent frame 32 generally includes a central annular portion 36, an atrial portion 38 extending from one end of the annular portion 36, and a ventricular portion 40 extending from the opposite end of the annular portion 36. Annular portion 36 is similar to the annular portion described above relative to FIGS. 1-4, except that the annular portion 36 has a wire arrangement that includes two members 42 on generally opposite sides of the annular portion 36 that are somewhat wider than the extending posts 18 of stent frame 10. These members 42 have a height that is greater than that of the remainder of the annular portion 36. The wire between each of the members 42 around the periphery of the annular portion 36 is arranged in a generally sinusoidal pattern. The atrial portion 38 includes a wire that is arranged to provide a series of flanges 44 that extend radially outward at an angle from one end of the annular portion 36. All of the flanges 44 are generally the same size and shape and extend at generally the same angle from the annular portion 36, although it is contemplated that the flanges 44 are configured differently from each other. Ventricular portion 40 includes a wire that is shaped to provide a first portion 46 that extends in generally the same longitudinal or axial direction as the annular portion 36 along a portion of its periphery, and at least one flange 48 that extends radially outward at an angle relative to the annular portion 36. First portion 46 may alternatively be flared at least slightly relative to the annular portion 36 in order to engage with the aortic leaflet, without substantially blocking the left ventricular outflow tract. First portion 46 is arranged as a series of sinusoidal peaks and valleys that are generally the same size and shape as each other, although it is contemplated that they are different from each other.

The stent frame 32 may include a number of wires or wire portions that are attached to each other generally as shown in the illustrated configuration, where one arrangement could include separate wires for each of the annular portion 36, the atrial portion 38, and the ventricular portion 40. Alternatively, the entire stent frame 32 may be cut from a single sheet of material such that the stent frame 32 is an integral structure that does not include individual components. The relative sizes and number of wire peaks, valleys, and flanges illustrated for each of the portions of the stent frame 32 are exemplary, and the construction can instead include different sizes, numbers, and configurations of these components. In addition, this embodiment of stent frame 32 can include any of the variations discussed above relative to stent frame 10, including a variation that includes three extending members 42 to accommodate the attachment of a tri-leaflet valve within the frame instead of the bi-leaflet attachment arrangement shown.

Stent assembly 30 further includes a covering material 34 that is attached to at least some of the wires of the stent frame 32, and may be attached to all of the wires or wire portions of stent frame 32, if desired. The covering material can be cut before or after attachment to the stent frame 32 to allow for a valve structure (not shown) to be attached to the stent frame 32 within the central area of the annular portion 36. The covering material 34 can be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. The covering material may be attached to its respective stent frame by sewing, adhesives, or other attachment methods.

FIGS. 10-13 illustrate a stent frame 60 in accordance with another embodiment of the invention that generally includes a central annular portion 62, an atrial portion 64 extending from one end of the annular portion 62, and a ventricular portion 66 extending from the opposite end of the annular portion 62. Annular portion 62 is similar to the annular portion described above relative to FIGS. 1-4 in that it includes a wire portion that is shaped to provide two extending posts 68 on generally opposite sides of the annular portion 62, and a generally sinusoidal pattern between each of its extending posts 68. In this embodiment, the annular portion 62 further includes V-shaped support members 70 that are arranged with the base of each "V" of the V-shaped members 70 generally coinciding with the base of an extending post 68. These V-shaped members 70 have a similar configuration to the extending members 42 of stent frame 32 in that the stent frame 60 includes a combination of extending posts 68 along with V-shaped members 70. These V-shaped members 70 can be used to provide additional structural integrity to the stent frame 60.

The atrial portion 64 includes a series of flanges 72 that extend radially outward at an angle from one end of the annular portion 62. All of the flanges 72 are shown as being generally the same size and shape and extend at generally the same angle from the annular portion 62, although it is contemplated that at least some of the flanges 72 are configured differently from each other. Ventricular portion 66 includes a wire that is arranged to provide a first portion 74 that extends in generally the same longitudinal or axial direction as the annular portion 62 along a portion of its periphery, and at least one flange 76 that extends radially outward at an angle relative to the annular portion 62. First portion 74 may be flared at least slightly relative to the annular portion 62 in order to engage with the aortic leaflet without substantially blocking the left ventricular outflow tract. First portion 74 is arranged as a series of sinusoidal peaks and valleys that are generally the same size and shape as each other, although it is contemplated that they are differently sized and/or shaped from each other.

The stent frame 60 may include a number of wires or wire portions that are attached to each other generally as shown in the illustrated configuration, where one arrangement could include separate wires for each of the annular portion 62, the atrial portion 64, and the ventricular portion 66. In one embodiment, the V-shaped members 70 are crimped to other wires of the stent frame 60. Alternatively, the entire stent frame 60 may be cut from a single sheet of material such that the stent frame 60 is an integral structure that does not include individual components. The relative sizes and number of wire peaks, valleys, and flanges illustrated for each of the portions of the stent frame 60 are exemplary, and the construction can instead include different sizes, numbers, and configurations of these components. In addition, this embodiment of stent frame 60 can include any of the variations discussed above relative to the stent frames described herein, including a variation that includes three extending posts 68 to accommodate the attachment of a tri-leaflet valve within the frame instead of the bi-leaflet attachment arrangement shown.

Figure 17:
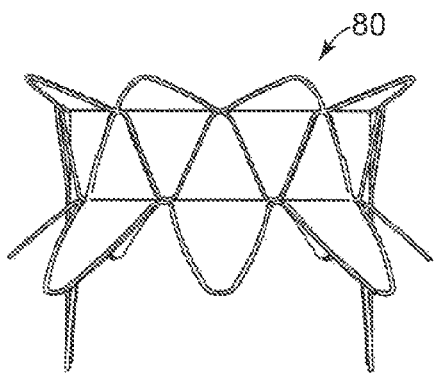
FIGS. 17 and 18 are different side views of the stent frame of FIG. 14.
Figure 18:
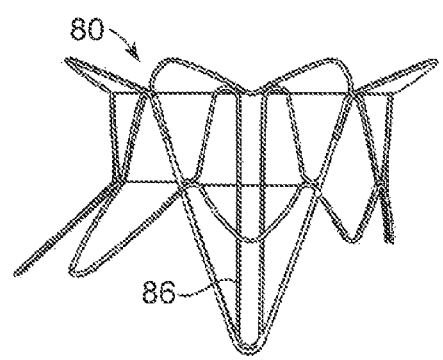
Figure 19:
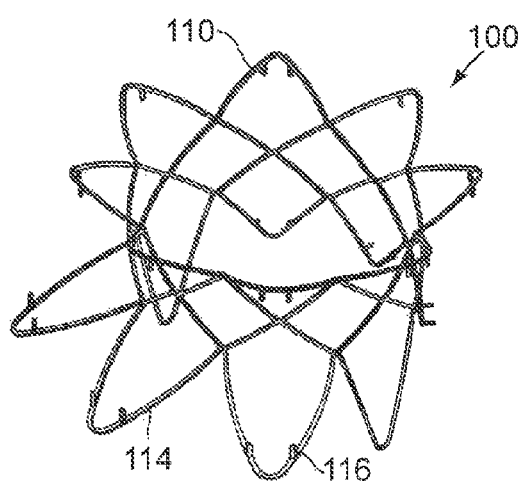
FIG. 19 is a perspective view of another stent frame in accordance with the invention.
Figure 20:
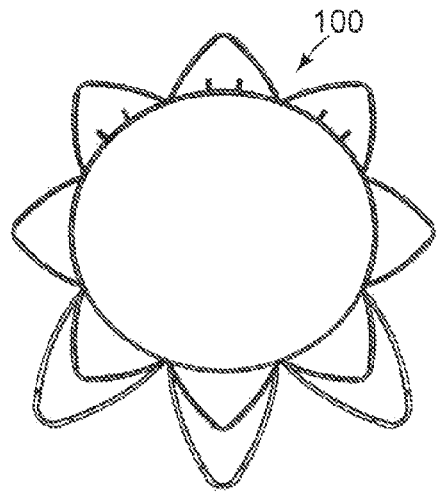
FIG. 20 is a top view of the stent frame of FIG. 19.

FIGS. 14-18 illustrate a stent assembly 80 that comprises a stent frame 82 that is generally similar to the stent frame 60 described above relative to FIGS. 10-13, and further including a covering material 84. As with the covering material 34 described above, covering material 84 can similarly include materials that facilitate at least some tissue ingrowth. The covering material 84 can be cut between extending posts 86 of stent frame 82, such as generally along cut line 88, to allow for attachment of a valve (not shown) that will be positioned within the interior area of the stent frame 82. This stent frame and assembly, along with many other stents of the invention, may be provided with portions that are made of self-expandable materials and other portions that are made of balloon-expandable materials. With particular reference to FIG. 17, for example, the atrial and ventricular portions may be made of a self-expanding material, while the central annular portion may be made of a balloon-expandable material to allow for high radial force at the annulus.

Figure 21:
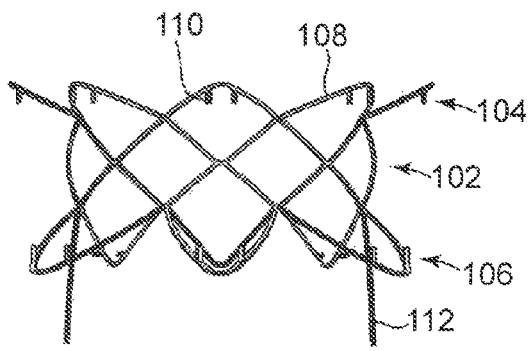
FIGS. 21 and 22 are different side views of the stent frame of FIG. 19.
Figure 22:
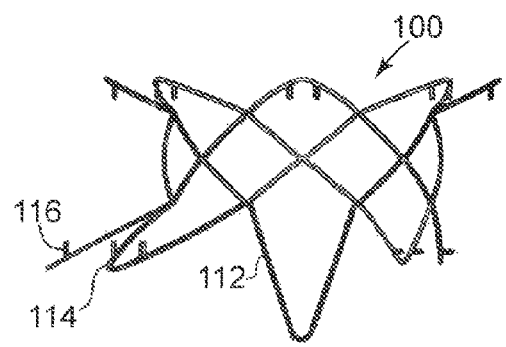

FIGS. 19-22 illustrate a stent frame 100 in accordance with another embodiment of the invention that generally includes an annular portion 102, an atrial portion 104 extending from one end of the annular portion 102, and a ventricular portion 106 extending from the opposite end of the annular portion 102. Annular portion 102 includes wire or wire portions that cross each other around the periphery of the stent frame 100 in a series of X-shaped structures. The stent frame 100 includes one or more wires shaped to provide a series of flanges 108 that extend radially outward at an angle from one end of the annular portion 102. All of the flanges 108 are shown as having generally the same size and shape and as extending at the same angle from the annular portion 102, although it is contemplated that the flanges 108 are configured differently from each other. At least some of the flanges 108 also include one or more barbs or extensions 110, where this illustrated embodiment includes two barbs 110 near the distal tip of each of the flanges 108. Each of the barbs 110 preferably extends from its respective flange 108 in such a way so that when the stent frame 100 is positioned relative to the annulus of a valve in which it will be implanted, the barbs 110 will be engageable with the tissue to which they are adjacent. Thus, as is best illustrated in FIGS. 21 and 22, barbs 110 extend downwardly or toward the annular portion 102 of the stent frame 100 so that they can engage with the structure of the heart when implanted. It is understood that the barbs 110 can have a different size, shape, orientation, positioning, etc. than shown, and that the each of the flanges 108 can include more or less than the two barbs 110 shown. Further, it is contemplated that only some of the flanges 108 include such barbs 110.

The ventricular portion 106 includes a wire that is shaped to provide two extending posts 112 on generally opposite sides of the stent frame 100, at least one flange portion 114 extending radially outward from annular portion 102 on one side of the stent frame 100 between extending posts 112, and a sinusoidal wire pattern on the other side of the stent frame 100 between extending posts 112. At least some of the flanges 114 also include at least one barb 116, where this illustrated embodiment includes two barbs 116 near the distal tip of each of the flanges 114. Each of the barbs 114 preferably extends from its respective flange 114 in such a way that when the stent frame 100 is positioned relative to the annulus of a valve in which it will be implanted, the barbs 116 will be engageable with the tissue to which they are adjacent. Thus, as is best illustrated in FIGS. 21 and 22, barbs 116 extend upwardly or toward the annular portion 102 of the stent frame 100. As with the barbs 110 described above, barbs 116 can have a different size, shape, orientation, positioning, etc. than shown, and each of the flanges 114 can include more or less than the two barbs 116 shown. Further, it is contemplated that only some of the flanges 114 include barbs 116.

Figure 23:
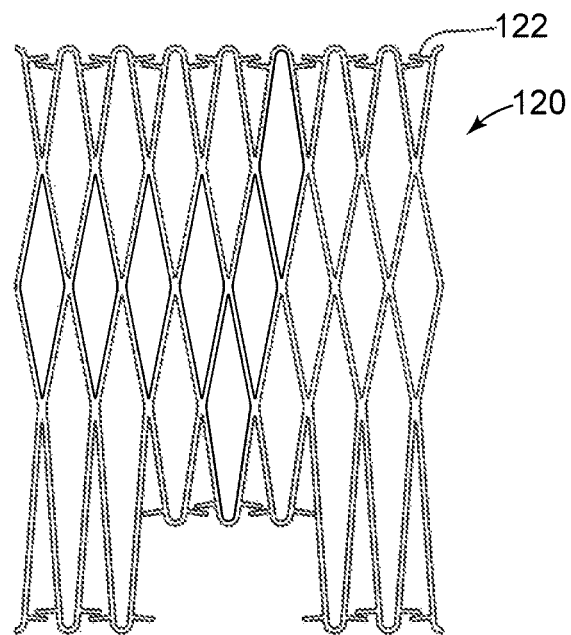
FIG. 23 is a side view of a pattern for a stent frame of the invention.

FIG. 23 illustrates an exemplary pattern 120 for a stent frame of the type illustrated above relative to FIGS. 19-22. This stent frame pattern 120 includes a diamond-shaped pattern that can be cut from a single sheet of material. The stent frame pattern 120 can be formed into a tubular shape to make a stent frame. As shown, this embodiment includes a number of barbs 122 extending from distal ends of the pattern.

Figure 24:
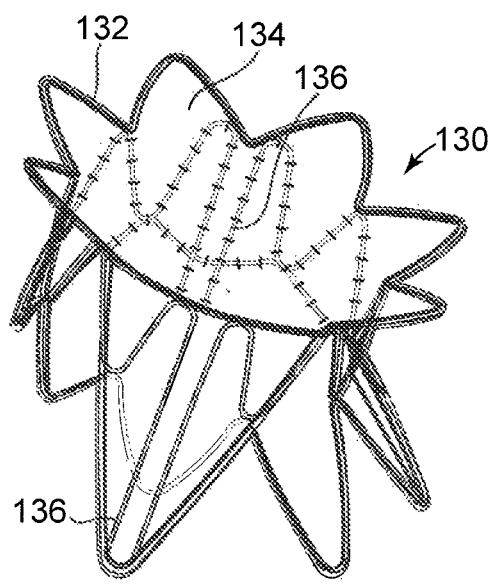
FIG. 24 is a perspective view of a stent frame of the invention with fabric attached.

FIG. 24 illustrates a stent assembly 130 of the invention, which includes a stent frame 132 and a covering material 134. As shown, the covering material 134 is stitched to the stent frame 132 along many of the wires of this assembly that are visible. This stent frame 132 includes two extending posts 136 positioned generally across from each other, which are provided as the commissure posts to which the leaflets of a valve assembly will be attached to provide a bi-leaflet valve.

Figure 25:
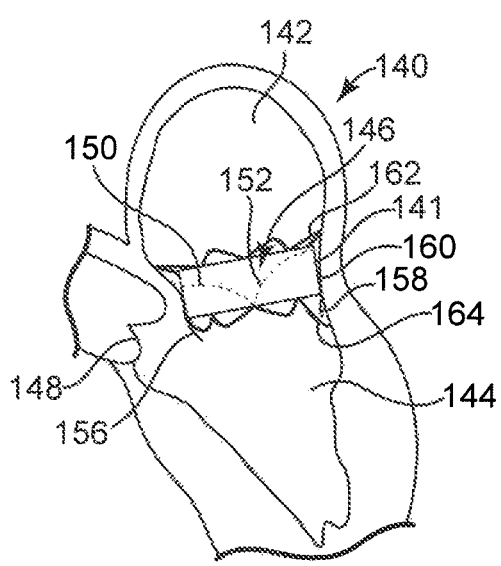
FIG. 25 is a schematic sectional view of a portion of a heart with a stent frame of the invention positioned within the annulus of a mitral valve.

FIG. 25 schematically illustrates a portion of a heart 140, with an exemplary stent assembly 141 of the invention positioned therein. In particular, heart 140 includes a left atrium 142, a left ventricle 144, a mitral valve 146 and an aortic valve 148. The broken lines of mitral valve 146 illustrate its native leaflets as they would generally be configured prior to implantation of stent assembly 141. In particular, mitral valve 146 includes a first leaflet 150 on the anterior side of the valve, and a second leaflet 152 on the posterior side of the valve. When the native mitral valve 146 is operating properly, the native leaflets 150, 152 will generally function in such a way that blood flows toward the left ventricle 144 when the leaflets 150, 152 are in an open position, and so that blood is prevented from moving toward the left atrium 142 when the leaflets 150, 152 are in a closed position. However, stent assembly 141 can be positioned in the area of mitral valve 146 when it is not functioning properly (to replace the mitral valve) in accordance with the invention, thereby pushing the leaflets 150, 152 out of the mitral valve space, such as are shown as displaced leaflets 156 and 158, respectively.

As shown, stent assembly 141 includes an annular portion 160, an atrial portion 162 including flares extending from one side of the annular portion 160 and toward the left atrium 142, and a ventricular portion 164 including flares extending from the posterior side of the annular portion 160 and toward the left ventricle 144. In order to not block the flow of blood through the aortic valve 148, the ventricular portion 164 of the stent assembly 142 that is closest to the aortic valve 148 does not have flares or has flares that have a minimal height. In this way, the stent assembly 142 will not push the leaflet 156 to a position in which it will interfere with blood flow through the aortic valve 148 and/or interfere with the actual movement or functioning of the leaflets of the aortic valve 148. However, annular portion 160 preferably has a sufficient length to provide a suitable area of contact with the annulus of the mitral valve to help to maintain it in its desired position.

As stated above, the stent assemblies of the invention can also be implanted for replacement of the tricuspid valve. In particular, if the stent assemblies of the invention are positioned within the annulus of a triscuspid valve, the atrial flares would be removed or made in such as way that they do not contact the apex of the triangle of Koch in order to not disturb the conduction system (i.e., the AV node and bundle of His). In addition, the ventricular flares would not contact the septal portion of the ventricle in order to not disturb the conduction system, wherein these flares can thus be similar to those described above relative to stent assemblies for the mitral area. In addition, the ventricular flares in this embodiment can generally resemble the posterior flares in an inferior and anterior direction (e.g., approximately ⅔ of the flares).

Stent frames of the type described above can be assembled into a stented valve assembly in accordance with the methods of the invention described herein, although such valves are not shown in the Figures. One exemplary method for assembling a stented valve generally first includes preparation of a porcine aortic valve, then a subsequent mounting or attachment of the prepared porcine valve to the stent frame using a variety of mounting or attachment techniques. Bi-leaflet, tri-leaflet, and other variations of valve assemblies can be attached within the stent frames described herein.

The various flange portions described above relative to the atrial portions and ventricular portions of the stent frames are generally shown as being V-shaped or U-shaped. However, the flange portions may instead be semi-circular, rectangular, oblong, or the like, and may be considerably smaller or larger than shown. In yet another variation, a different flange structure that is more continuous around the periphery of the annular portion of the stent frame can be used (i.e., the flange structure does not comprise a series of adjacent flanges but instead comprises more of a continuous flared structure at one or both ends of the stent frame). In any case, the flange portion(s) are preferably configured to be a shape and size that can provide an anchoring function for the stent assembly when it is positioned to replace a valve. For example, if stent assembly were positioned within the mitral valve annulus any flange portions that extend from the stent assembly on the atrial side can provide interference with the walls of the left atrium, thereby inhibiting motion of the stent assembly.

Figure 26:
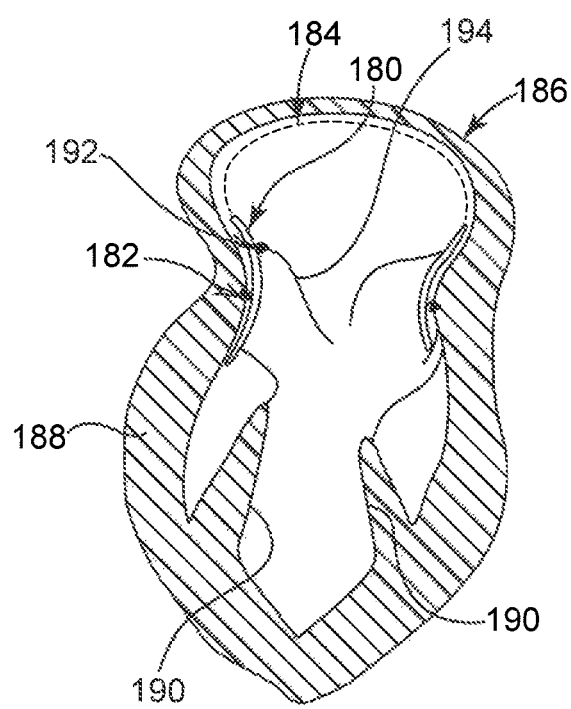
FIG. 26 is a schematic front view of a portion of a heart with an exemplary stent of a transcatheter valve positioned relative to a native valve annulus.

The atrial flares or flange portions can also incorporate features that enable the stent to be sewn in place as part of an atrial incision closure using various means, such as clips, sutures, and the like. In addition, if the atrial flares or flange portions of a stent progress further upward toward the top of the atrium, the result can provide enhanced stabilization of the prosthesis. One example of a configuration of a stent frame 180 that provides such a stabilization feature is illustrated in FIG. 26. This and other stent frames comprising stabilization features can engage the native anatomy of the atrium for stable position and fixation of a replacement valve. This concept can be applicable to transcatheter or minimally invasive replacement of an insufficient or stenotic mitral or tricuspid valve. Such stent frames generally include a stent inflow aspect member or members that extend beyond the native valve annulus to match the curvature of the atrium. These members can have a variety of shapes and configurations, but generally all function to prevent antegrade and/or retrograde migration of the valve assembly. The degree of protrusion into the atrium can vary, but can advantageously extend past the inflection point of the radius of curvature. The members can also extend all the way to the top of the atrium, if desired. The members can be discrete or joined at the top of the atrium to generally match the shape of the anatomy. Various covering materials can be used to cover or partially cover the stabilization portion of the stent frame, including materials such as fabric, polymer, tissue, or other biocompatible materials. The material can further be chosen to enhance in-growth and/or to reduce abrasion and trauma, if desired.

In the exemplary embodiment of FIG. 26, a stent frame 180 is shown as positioned relative to the annulus 182 of a native valve, and a hoop or series of hoops 184 (indicated by the broken line in atrium 186) extends from a top end of the stent frame 180 into the atrium 186, which provides additional stabilization of the stent and can help to minimize stent migration. Referring still to FIG. 26, a schematic view of a portion of a heart is shown, including the left ventricle 188, atrium 186, papillary muscles 190, and the annulus 182 of the native valve. A valve comprising a stent frame 180 of the invention is shown as positioned so that its annulus 192 is at least slightly higher than the annulus 182 of the native valve. Two exemplary leaflets 194 are shown as extending from the frame 180 at the position of its annulus 192. This positioning of the stent frame 180 can reduce its protrusion into the left ventricle 188, which can thereby minimize contact and rubbing of the stent frame 180 on the wall of the left ventricle 188 and papillary muscles 190. The position of the stent frame 180 can also reduce the potential for erosion, arrhythmias and ischemia.

Figure 27:
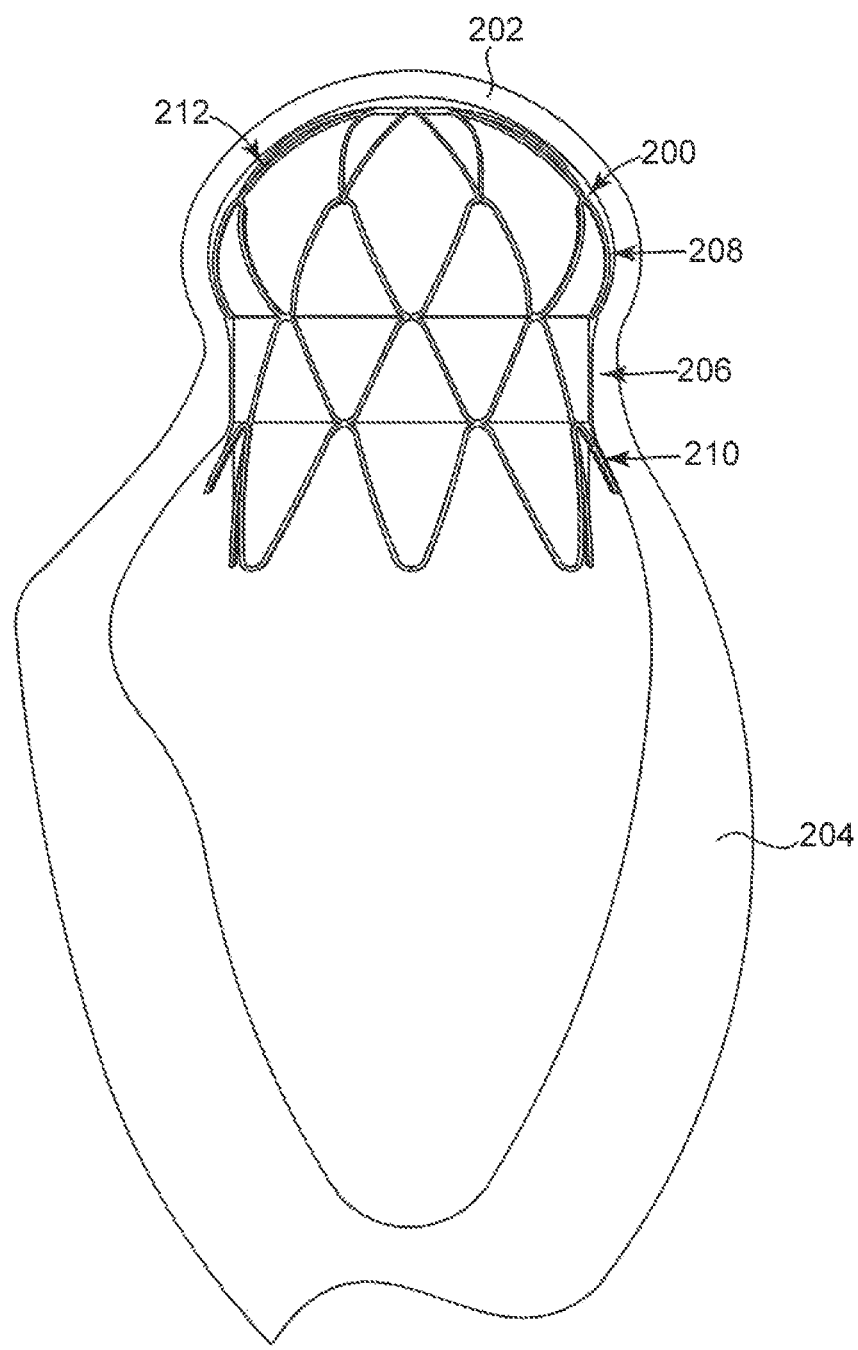
FIG. 27 is a schematic front view of a portion of a heart with an exemplary stent frame positioned relative to a native valve annulus.
Figure 28:
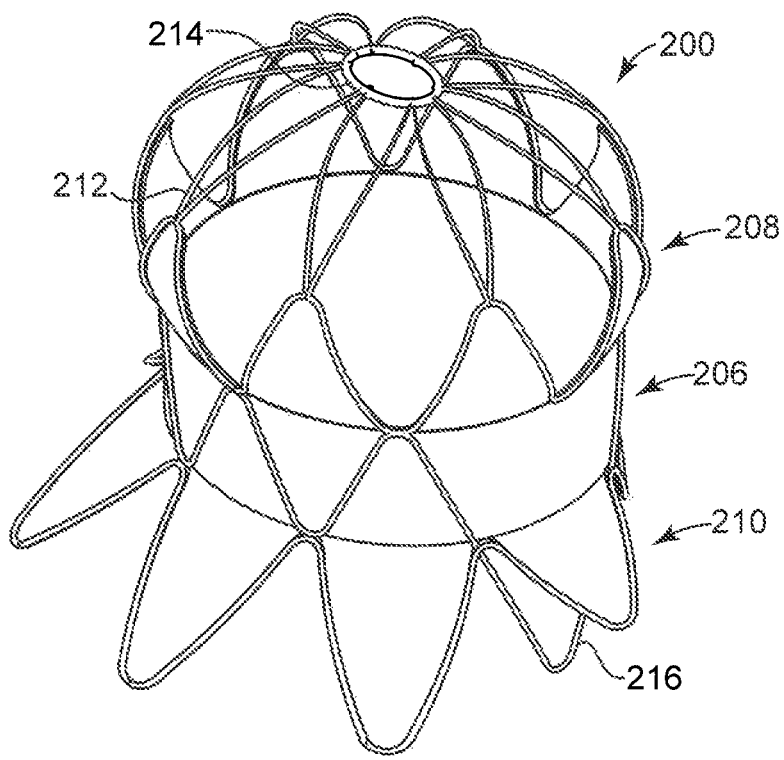
FIG. 28 is a perspective view of the stent frame of FIG. 27.
Figure 29:
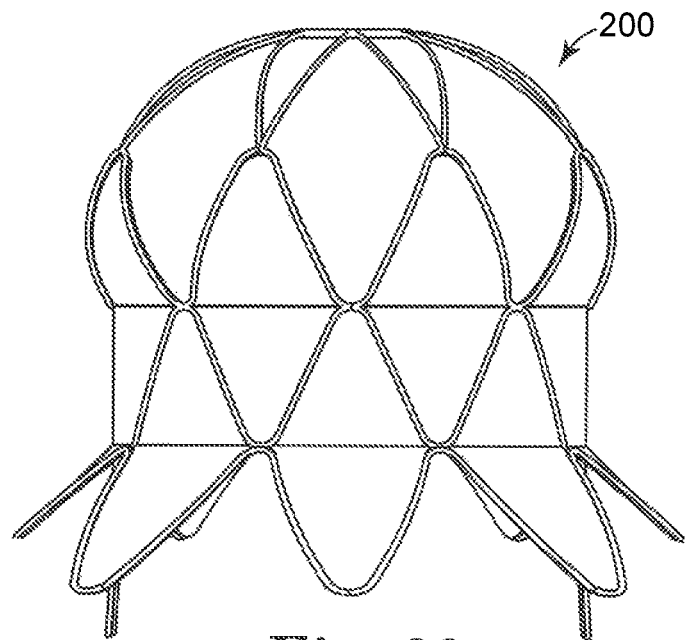
FIG. 29 is a side view of the stent frame of FIGS. 27 and 28.

FIGS. 27-29 illustrate another embodiment of a stent frame 200 providing the features described above for positioning and fixation relative to a native valve annulus. FIG. 27 shows this stent frame 200 positioned relative to an atrium 202 and ventricle 204. Stent frame 200 includes an annular portion 206, an atrial portion 208, a ventricular portion 210, and a securing portion 212 extending from the atrial portion 208. Securing structure 212 generally includes a series of wires arranged in petals or another configuration that extends from the peaks of the wires of the atrial portion 208. The petals are attached at their distal ends to a disc 214 or other structure that maintains the wires in a dome-type shape, as shown. The ventricular portion 210 can include any of the features described above relative to the ventricular end of the stent frames, wherein this particular embodiment shows a ventricular portion having flares that extend outwardly relative to a central longitudinal axis of the stent frame 200. The annular portion 206 further includes two extending posts 216 that are at least somewhat taller or longer than the height of the structure of the annular portion between the extending posts.

Figure 30:
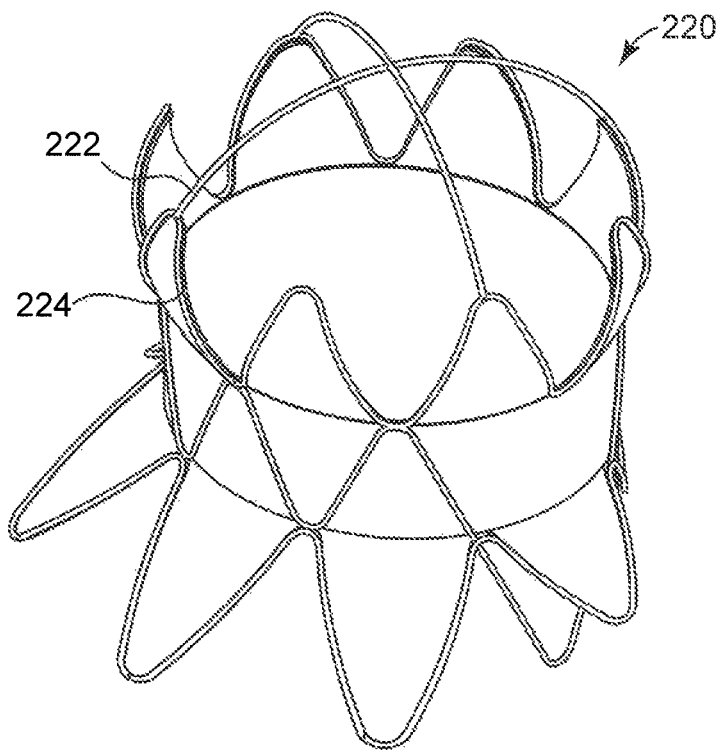
FIG. 30 is a perspective view of another exemplary stent frame.
Figure 31:
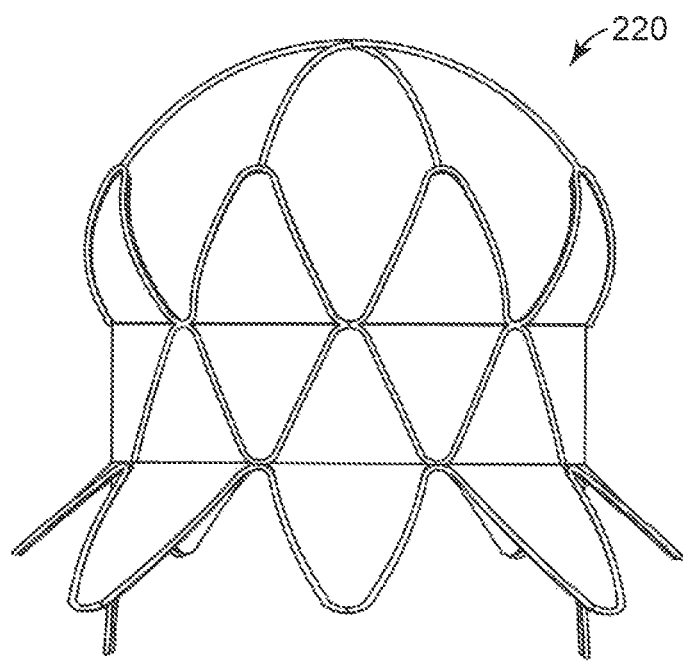
FIG. 31 is a side view of the stent frame of FIG. 30.
Figure 32:
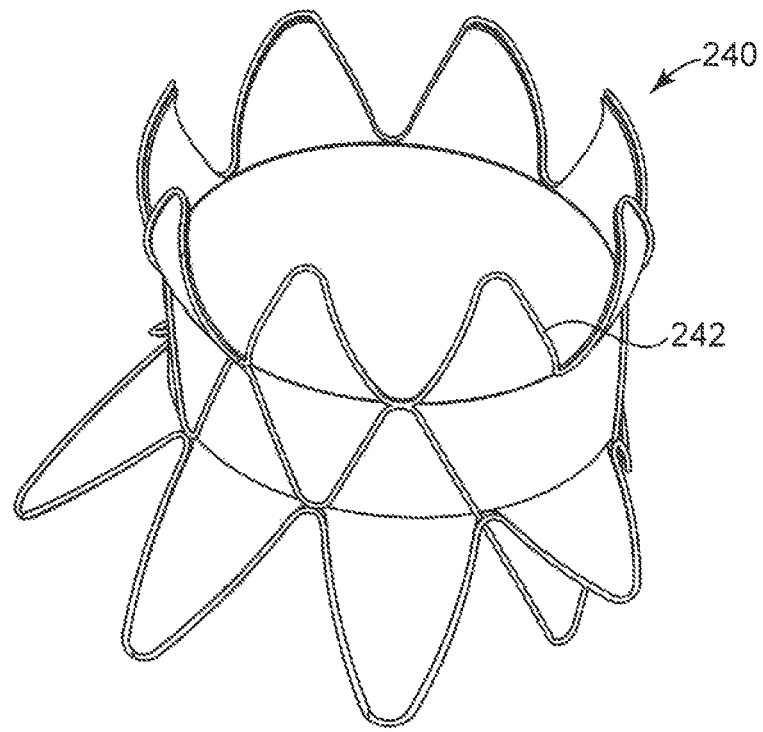
FIG. 32 is a perspective view of another exemplary stent frame.
Figure 33:
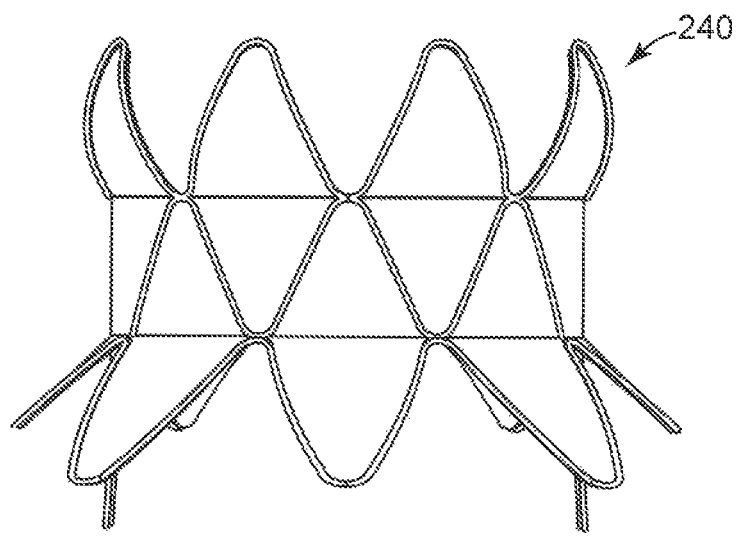
FIG. 33 is a side view of the stent frame of FIG. 32.

FIGS. 30 and 31 illustrate another embodiment of a stent frame 220 that also includes an atrial portion 224 comprising a series of flares that are curved at least slightly toward a central longitudinal axis of the stent frame. The frame 220 further includes at least two support wires 222 that form an additional securing structure of this embodiment. As shown, this exemplary embodiment illustrates two wires 222, each of which extends between two atrial flares on opposite sides of the frame, thereby helping to maintain the flares in this configuration and providing a dome-shaped support structure. However, it is contemplated that the stent frame 220 instead includes more or less than two wires. Further, it is contemplated that wires extend from only some of the flares of the atrial portion 224, as shown, or that all of the flares of the atrial portion 224 are connected to another flare with a support wire 222. In yet another embodiment, which is illustrated in FIGS. 32 and 33, a stent frame 240 includes an atrial portion 242 having multiple flares that are curved somewhat toward a central longitudinal axis of the stent frame 240. However, this exemplary embodiment does not also include any additional connecting wires between the flares.

Figure 34:
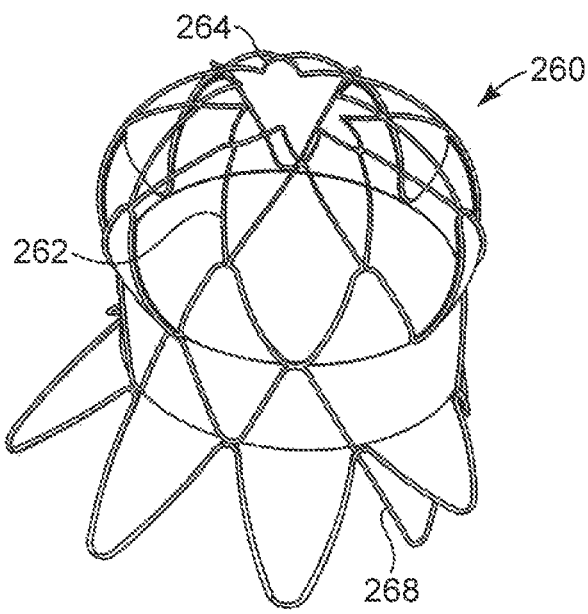
FIG. 34 is a perspective view of another exemplary stent frame.
Figure 35:
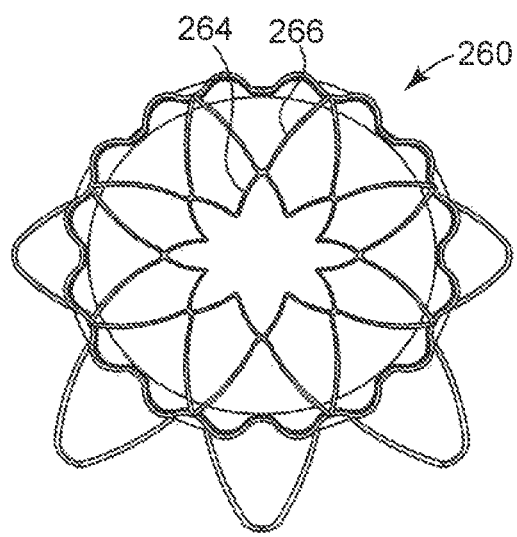
FIG. 35 is a top view of the stent frame of FIG. 34.
Figure 36:
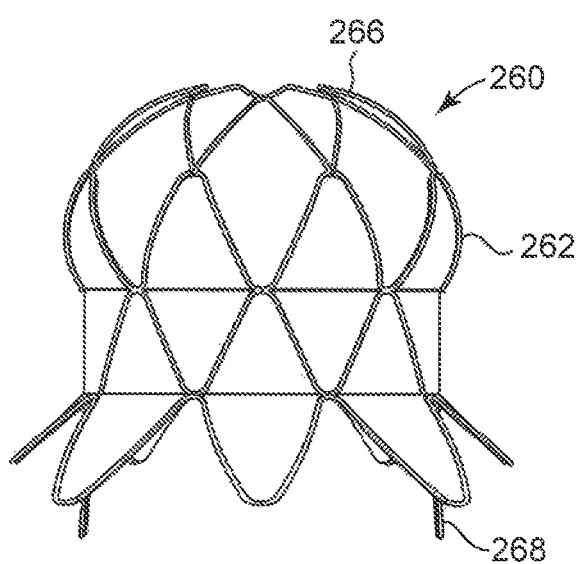
FIG. 36 is a side view of the stent frame of FIG. 34.

FIGS. 34-36 illustrate yet another embodiment of a stent frame 260 that includes an atrial portion comprising flares 262 and a series of wires 266 extending from the flares 262 toward a central longitudinal axis of the stent frame. The wires 266 are arranged as petals or another configuration that extends from the peaks of the wires of the atrial portion. The wires 266 are attached at their distal ends to a structure 264 that maintains the wires in a dome-type shape, as shown. The ventricular portion of the stent frame 260 can include any of the features described above relative to the ventricular end of the stent frames, wherein this particular embodiment shows a ventricular portion having flares that extend outwardly relative to a central longitudinal axis of the stent frame. The annular portion further includes two extending posts 268 that are at least somewhat taller or longer than the height of the structure of the annular portion between the extending posts.

Any of the embodiments of stent assemblies described herein relative to the invention may include a gasket or other member around its exterior to provide for sealing against paravalvular leakage and to facilitate pannus in-growth for stabilization of the stent. Such a gasket or other member may alternatively or additionally be positioned on the interior portion of the stent or on the underside of a cuff provided on the stent.

In addition, it is contemplated that the ventricular flares associated with the stented valves of the invention can house biologics to target infarcts (stem cells, genes, proteins, etc.), which are often located posterior-inferiorly in patients with ischemic mitral regurgitation. The areas of the stented valves of the invention used for anchoring could also be seeded with cells or biologics to promote ingrowth for quick incorporation into the surrounding tissue. This could aid in eliminating paravalvular leakage and in eliminating migration or embolization of the prosthesis. In one example for a mitral valve replacement, the atrial and annular portions can include pro-ingrowth biologics and the ventricular portion can include therapeutic biologics and/or pro-ingrowth biologics.

The stent assemblies of the present invention may be positioned within the desired area of the heart via entry in a number of different ways. In one example, the stent assembly may be inserted transatrially, where entry may be done either percutaneously or in a minimally invasive technique on a beating heart in which access is through the side of the heart, or even through a standard open heart valve replacement procedure using heart-lung bypass and sternotomy where the described device would be used as an alternative to the standard replacement. In another example, the stent assembly may be inserted transapically, where entry again may be done either percutaneously or in a minimally invasive technique on a beating heart in which access is through the side of the heart. In yet another example, the stent assembly may be inserted transeptally, where entry can be done percutaneously.

The invention further includes a method of positioning a valve into a body lumen, such as one of the atrioventricular valve openings of the heart. The method comprises the steps of compressing a stent frame of a stented valve, wherein the stent frame includes an annular region, an atrial portion extending from one end of the annular region, and a ventricular portion extending from the other end of the annular region. A sheath or other component of a delivery system can be slid or otherwise positioned over the compressed stented valve to keep it from expanding and to minimize interference between the stented valve and the vasculature through which it will be traveling. The stented valve is then delivered to the annulus of the desired valve area of the patient, which delivery may be performed transapically, for example. In one method, the valve is accessed through the bottom of the valve. When the valve is in position, the atrial region or portion of the stent is released, such as by retracting the sheath of the delivery system by a sufficient amount that this portion of the stented valve is exposed. Due to the self-expanding properties of the stent frame, the atrial portion will expand outwardly relative to the sheath in which it was enclosed. The delivery system is then used to pull the stent valve back against the annulus to engage the atrial portion of the stent with the annulus. The sheath of the delivery system can then be further retracted to release the ventricular portion of the stent frame from the delivery system. Due to the self-expanding properties of the stent frame, the ventricular portion will expand outwardly relative to the sheath in which it was enclosed. The delivery system can then be retracted from the patient.

The present invention has now been described with reference to several embodiments thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A stent frame comprising:
 an annular portion comprising:
  a longitudinal axis,
  at least two extending posts, and
  a generally sinusoidal structure of peaks and valleys between each of the at least two extending posts, the generally sinusoidal structure having first and second ends,
  wherein the generally sinusoidal structure has a generally constant height and
  wherein, in an expanded state, each of the extending posts extends in a direction that is generally parallel to the longitudinal axis and has a height that is greater than the generally constant height of the generally sinusoidal structure of the annular portion;
 an atrial portion extending from the first end of the generally sinusoidal structure, wherein the atrial portion comprises:
  a plurality of flares that extend radially outward relative to the longitudinal axis of the annular portion, and
  a dome-type structure extending from the plurality of flares; and
 a ventricular portion extending from the second end of the generally sinusoidal structure, wherein the ventricular portion comprises:
  at least one flare that extends radially outward relative to the longitudinal axis of the annular portion, and
  a first portion that extends from the second end of the generally sinusoidal structure, the first portion having a height that is smaller than a height of the at least one flare of the ventricular portion.

2. The stent frame of claim 1, wherein the stent frame is compressible and expandable for percutaneous delivery and implantation into a body lumen.

3. The stent frame of claim 1, wherein at least one of the annular portion, the atrial portion, and the ventricular portion comprises a shape memory material.

4. The stent frame of claim 1, wherein each of the flares of the atrial portion has a first end that extends from a peak of the annular portion and a second end that extends from an adjacent peak of the annular portion.

5. The stent frame of claim 1, wherein each of the at least two extending posts extends from two adjacent peaks of the annular portion and toward the ventricular portion of the stent frame.

6. The stent frame of claim 1, wherein the annular portion, the atrial portion, and the ventricular portion comprise an integral structure.

7. The stent frame of claim 1, wherein the height of each of the extending posts is greater than the distance between the peaks and valleys of the generally sinusoidal structure.

8. The stent frame of claim 7, wherein a first extending post of the at least two extending posts comprises a base that is spaced at a furthest distal point of the stent frame from the atrial portion of the stent frame, and further comprising a first support member comprising a first end that extends from the generally sinusoidal structure, a second end that extends from the generally sinusoidal structure, and a base between its first and second ends that is adjacent to the base of the first extending post.

9. The stent frame of claim 1, further comprising a covering material extending across a width of each of the extending posts, and wherein the covering material comprises a cut line within the width of the extending post.

10. The stent frame of claim 1, wherein each of the annular portion, the atrial portion, and the ventricular portion comprises a separate wire.

11. The stent frame of claim 1, wherein the dome-type structure comprises a series of wires.

12. The stent frame of claim 11, wherein distal ends of the series of wires are connected to a maintaining structure that maintains the series of wires in a dome-type shape.

13. The stent frame of claim 1, wherein the first portion extends radially outward relative to the longitudinal axis of the annular portion.

14. The stent frame of claim 1, wherein the first portion generally follows an outer periphery of the annular portion.

15. The stent frame of claim 1, wherein the plurality of flares of the atrial portion are configured to engage a first side of an annulus in which the stent frame is implanted, and wherein the at least one flare of the ventricular portion is configured to engage a second side of the annulus that is opposite of the first side.

16. A valve prosthesis comprising:
a stent frame comprising:
an annular portion comprising:
a longitudinal axis,
at least two extending posts, and
a generally sinusoidal structure of peaks and valleys between each of the at least two extending posts, the generally sinusoidal structure having first and second ends,
wherein the generally sinusoidal structure has a generally constant height and
wherein, in an expanded state, each of the extending posts extends in a direction that is generally parallel to the longitudinal axis and has a height that is greater than the generally constant height between each of the extending posts of the generally sinusoidal structure of the annular portion;
an atrial portion extending from the first end of the generally sinusoidal structure, wherein the atrial portion comprises:
a plurality of flares that extend radially outward relative to the longitudinal axis of the annular portion as the plurality of flares extend away from the annular portion, and
a dome-type structure extending from the plurality of flares;
a ventricular portion extending from the second end of the generally sinusoidal structure, wherein the ventricular portion comprises:
at least one flare that extends radially outward relative to the longitudinal axis of the annular portion, and
a first portion that extends from the second end of the generally sinusoidal structure, the first portion having a height that is smaller than a height of the at least one flare of the ventricular portion; and
a prosthetic valve comprising a first leaflet attached to two adjacent extending posts of the at least two extending posts within an interior area of the stent frame, and a second leaflet attached to two adjacent extending posts of the least two extending posts within the interior area of the stent frame,
wherein the extending posts of the annular portion are aligned with commissures of the prosthetic valve.

17. The valve prosthesis of claim 16, wherein the dome-type structure comprises a series of wires.

18. The valve prosthesis of claim 17, wherein distal ends of the series of wires are connected to a maintaining structure that maintains the series of wires in a dome-type shape.

19. The valve prosthesis of claim 16, wherein the first portion extends radially outward relative to the longitudinal axis of the annular portion.

20. The valve prosthesis of claim 16, wherein the first portion generally follows an outer periphery of the annular portion.

21. The valve prosthesis of claim 16, wherein the plurality of flares of the atrial portion are configured to engage a first side of an annulus in which the stent frame is implanted, and wherein the at least one flare of the ventricular portion is configured to engage a second side of the annulus that is opposite of the first side.

22. The valve prosthesis of claim 16, wherein:
the annular portion comprises at least three extending posts; and
the prosthetic valve further comprises a third leaflet attached to two adjacent extending posts of the at least three extending posts within the interior area of the stent frame.

23. The valve prosthesis of claim 16 further comprising a covering material attached to at least a portion of at least one of the annular portion, the atrial portion, and the ventricular portion.

* * * * *